United States Patent [19]

Brown

[11] Patent Number: 5,444,168
[45] Date of Patent: Aug. 22, 1995

[54] PROCESS FOR THE PRODUCTION OF SYMMETRICAL ETHERS FROM SECONDARY ALCOHOLS

[75] Inventor: Stephen H. Brown, Princeton, N.J.

[73] Assignee: Mobil Oil Corporation, Fairfax, Va.

[21] Appl. No.: 242,989

[22] Filed: May 16, 1994

[51] Int. Cl.$^6$ ............................................. C07C 41/09
[52] U.S. Cl. ...................................... 568/664; 568/698
[58] Field of Search ............................. 508/664, 698

[56] References Cited

U.S. PATENT DOCUMENTS

| | | | |
|---|---|---|---|
| 3,033,778 | 5/1962 | Frilette | 568/698 |
| 3,036,134 | 5/1962 | Mattox | 568/698 |
| 4,042,633 | 8/1977 | Woods | 568/698 |
| 4,380,657 | 4/1983 | Slaugh | 568/698 |
| 4,579,984 | 4/1986 | Neir et al. | 568/698 |
| 4,857,664 | 8/1989 | Huang et al. | 568/695 |
| 4,886,918 | 12/1989 | Sorgensen | 568/698 |
| 4,918,244 | 4/1990 | Nelson et al. | 568/698 |
| 4,967,020 | 10/1990 | Marler et al. | 568/698 |
| 5,099,072 | 3/1992 | Knifton | 568/698 |
| 5,220,078 | 6/1993 | Knifton et al. | 568/698 |
| 5,300,697 | 4/1994 | Knifton et al. | 568/698 |

FOREIGN PATENT DOCUMENTS

| | | | |
|---|---|---|---|
| 0407038 | 1/1991 | European Pat. Off. | 568/698 |
| 0595567 | 5/1994 | European Pat. Off. | 568/698 |
| 57-7432 | 1/1982 | Japan | 568/698 |

*Primary Examiner*—James H. Reamer
*Attorney, Agent, or Firm*—A. J. McKillop; M. D. Keen

[57] ABSTRACT

Secondary alcohols are converted to symmetrical secondary alkyl ethers in high selectivity. The method employs acidic solid metallosilicate catalyst particles to accomplish the etherification by selective intermolecular dehydration of secondary alcohol to form di-secondary alkyl ethers. Preferably, the catalysts are solid shape selective aluminosilicate particles, especially zeolite such as ZSM-5, zeolite HY and zeolite Beta. Continuous separation of by-product olefin and ether during the etherification reaction improves selectivity.

9 Claims, No Drawings

PROCESS FOR THE PRODUCTION OF SYMMETRICAL ETHERS FROM SECONDARY ALCOHOLS

This invention relates to the production of ethers by dehydration of alcohols or alkanols. The invention particularly relates to a method for the selective production of symmetrical ethers from secondary aliphatic alkanols. The invention especially relates to a method for the preparation of di-secondary alkyl ethers with high selectivity employing acidic zeolite catalysts.

BACKGROUND OF THE INVENTION

The general processes employed in the prior art for the preparation of ethers include the dehydration of alcohols, the addition of primary alcohols to alkenes, and reaction between an alkyl halide and a sodium alkoxide or sodium phenoxide (Williamson synthesis). Dehydration of alcohols with acidic catalysts produces ethers by intermolecular dehydration and olefins by intramolecular dehydration. Dehydration of mixed alcohols, it is known in the art, produces mixtures of all possible ethers with no particular selectivity. For secondary alcohols, acid catalyzed dehydration using classical acids such as sulfuric acid can proceed to form a symmetrical di-secondary alkyl ether of the starting secondary alcohol, an olefin, water, and an isomer of the starting secondary alcohol by olefin isomerization followed by hydration.

In view of the multiplicity of possible reaction pathways, the acid catalyzed preparation of symmetrical di-alkyl ethers from secondary alcohols is known to proceed in the prior art with very low selectivity. Further, with increasing alcohol carbon number, i.e., $C_4'$, classical acid catalyzed dehydration of secondary alcohols in the prior art proceeds ever more preferentially toward intramolecular dehydration to form olefins with an ever decreasing selectivity for the formation of the symmetrical di-secondary alkyl ether of the starting secondary alcohol. Primary literature references substantiate the poor ether selectivity obtained by acid catalyzed reaction of secondary alcohols (N. L. Drake and F. P. Veitch, The Action of Sulfuric Acid on Butanol-2, JACS, 57, 2623, 1935 and Patai, The Chemistry of the Ether Linkage, Interscience Publishers, NY, 1967, p.458).

It has come to pass that ethers are receiving renewed attention as components of gasoline blends, stimulated in part by the goals of the 1990 Clean Air Act. The dominant approach is to combine methanol with isobutylene or isoamylene to produce methyl tertiary butyl (MTBE) and tertiary amyl methyl ether (TAME) for gasoline blends. However, the petroleum feedstreams rich in tertiary olefins for MTBE or TAME synthesis are also rich in linear olefins. Upgrading these linear olefins to more economically valuable components such as secondary ethers to be employed, inter alia, as gasoline blending components would significantly improve overall process economics. It is known that these linear olefins can be converted to secondary alcohols by hydration. Conversion of the secondary alcohols to ethers, particularly symmetrical di-secondary alkyl ethers at high selectivity, would fulfill the need to maximize the utilization of linear olefins for ether production and provide a means to economically manufacture symmetrical di-secondary alkyl ethers not readily available by others processes.

Accordingly, it is an objective of the present invention to provide a process for the production of symmetrical di-secondary alkyl ethers from secondary alcohols.

It is a further objective of the present invention to provide a process for the production of symmetrical di-secondary alkyl ethers from secondary alcohols with high selectivity employing acid metallosilicate particles as catalyst.

SUMMARY OF THE INVENTION

A method has been discovered for the production of symmetrical secondary alkyl ethers in high selectivity from secondary alcohols. The method employs acidic solid metallosilicate catalyst particles to accomplish the etherification by selective intermolecular dehydration of secondary alcohol to form di-secondary alkyl ethers. Preferably, the catalysts are solid shape selective aluminosilicate particles, especially high silica-alumina zeolites such as zeolite Beta.

More particularly, the invention comprises a process for the production of symmetrical secondary ether(s) with high selectivity from secondary alkanol(s) comprising contacting the alkanols with solid, metallosilicate catalyst particles in an etherification zone under etherification conditions and recovering symmetrical di-alkyl secondary ethers as a reaction product. The secondary alkanols are selected from the group consisting of secondary cycloalkanol and secondary $C_3$–$C_{20}$ acyclic alkanol, substituted or unsubstituted.

Preferably, the ethers of the present invention are prepared from $C_4$–$C_{20}$ secondary alkanol.

DETAILED DESCRIPTION OF THE INVENTION

Secondary alcohols useful in the present invention include isopropanol and all $C_3$–$C_{20}$ monohydric alcohols containing at least one hydroxy methine group, $=CHOH$. The secondary alcohols have the formula $R_1R_2(CHOH)_x$ wherein $R_1$ and $R_2$ are alike or different and where x is the integer 1 when $R_1$ and $R_2$ are monovalent aliphatic or aromatic hydrocarbon radicals; or when $R_1$ and $R_2$ together comprise a single divalent alkenyl radical, substituted or unsubstituted. Preferred aliphatic radicals include $C_1$–$C_{19}$ normal alkyl and especially lower alkyl including methyl, ethyl, n-propyl, isobutyl, isopentyl, neopentyl and isohexyl. Preferred aromatic radicals include phenyl, phenylene, tolyl, tolylene, xylyl, xylylene and benzyl. Preferred alkenyl radicals include pentenyl and butenyl. Preferred alkanols comprise $C_4+$ secondary alkanols to provide $C_8+$ symmetrical ethers.

Symmetrical secondary ethers are those wherein two molecules of the same secondary alcohol condense by intermolecular dehydration to produce one molecule of symmetrical secondary ether and one molecule of water.

In general, catalysts useful in the present invention for the selective production of symmetrical ethers preferably embrace one category of zeolite, ZSM-5, for etherification of cyclopentanol to di-cyclopentyl ether and the large pore zeolites, as represented by zeolite Y and Beta, which are preferred for etherification of acyclic secondary aliphatic alkanols. The zeolites will possess a framework silica-to alumina ratio of greater than about 7.

For purposes of this invention, the term "zeolite" is meant to include the class of porotectosilicates, i.e., porous crystalline silicates, which contain silicon and oxygen atoms as the major components. Other components can be present in minor amounts, usually less than 14 mole %, and preferably less than 4 mole %. These components include aluminum, gallium, iron, boron, and the like, with aluminum being preferred.

Useful zeolite catalysts of the intermediate pore size variety, and possessing a Constraint Index of greater than about 2 up to about 12, include such materials as ZSM-5, ZSM-11, ZSM-23, and ZSM-35.

ZSM-5 is more particularly described in U.S. Reissue Pat. No. 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

ZSM-22 is more particularly described in U.S. Pat. No. 4,046,859, the entire contents of which is incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

The large pore zeolite with a framework silica-to-alumina ratio of greater than about 7 which are useful as catalysts in the process of this invention, i.e., those zeolite having a Constraint Index of no greater than about 2, are well known to the art. Representative of these zeolite are zeolite Beta, ultrastable zeolite Y (USY), dealuminized Y (Deal Y), mordenite, ZSM-3, ZSM-4, ZSM-12, ZSM-20, ZSM-50 and mixtures of any of the foregoing. Although zeolite Beta has a Constraint Index of about 2 or less, it should be noted that this zeolite does not behave exactly like other large pore zeolite. However, zeolite Beta does satisfy the requirements for a catalyst of the present invention.

Zeolite Beta is described in U.S. Reissue Pat. No. 28,341 (of original U.S. Pat. No. 3,308,069), to which reference is made for details of this catalyst.

Zeolite L is described in U.S. Pat. No. 3,216,789, to which reference is made for the details of this catalyst.

Zeolite Y is described in U.S. Pat. No. 3,130,007, to which reference is made for details of this catalyst.

A convenient measure of the extent to which a zeolite provides controlled access to molecules of varying sizes to its internal structure is the aforementioned Constraint Index of the zeolite. The method by which Constraint Index is determined is described fully in U.S. Pat. No. 4,016,218, to which reference is made for details of the method.

The acidic etherification process of the instant invention can be carried out in a batch type reactor or in a fixed bed, continuous flow reactor. The process etherification conditions comprise temperature between 20° C. and 300° C., pressure between 15 psi (105 kPa) and 1000 psi (7000 kPA) and weight hourly space velocity (WHSV) between 0.01 and 1.0. Preferably, the temperature is between 75° C. and 175° C. and the pressure is autogenous pressure. Solvents can be used in the process, preferably solvents such as alkanes that are unreactive, or the process can be carried out neat.

The discoveries inherent in the invention reveal that certain zeolites can catalyze the reaction of secondary alcohols to symmetrical ethers. These discoveries are particularly distinguished by the finding of the ability of the zeolite catalysts to achieve symmetrical secondary ether production at a selectivity of more than an order of magnitude greater than that found in the prior art. In that art, more traditional acid catalysts promote alcohol dehydration to olefin and water leading to a lower selection for the formation of secondary ether from the starting secondary alcohol. Olefin isomerization subsequent to the dehydration of secondary alcohol leads to the formation of isomeric secondary alcohols by olefin hydration. These alcohol isomers then react to produce isomeric secondary ethers by intermolecular dehydration.

The foregoing reactions of secondary alcohol intramolecular dehydration to olefin followed by secondary alcohol isomer production have been found to be repressed in the instant invention when the etherification reaction is carried out with the specified zeolite catalysts. It is thought that the shape selective nature of the preferred acidic zeolites serves to restrict reactions that are competitive with the formation of the secondary ether of the starting secondary alcohol. Certainly, it is the use of the preferred acidic zeolite etherification catalysts that accounts for the unexpected increase in secondary ether production selectivity as found in the process of the instant invention. Although many acid catalysts have been used in the prior art for the production of di-isopropyl ether from isopropanol, the instant invention represents the initial discovery wherein $C_4+$ alcohols have been converted to symmetrical ethers in high yields.

A concomitant advantage provided by the process of the present invention is an increase in stereoselectivity for the production of symmetrical secondary alkyl ethers. Reactions can be run under conditions that remove olefin formed by dehydration as fast as it is formed. The reaction is therefore run under kinetic control and the complications caused by olefin reactions—isomerization, hydration, and etherification—are avoided. As shown in the examples presented herein, when the process of the invention is followed, 2-pentanol is converted only to the 2,2-di-sec-pentyl ether. None of the 2,3 and 3,3 ethers are formed.

Although the efficacy of acidic zeolite catalyst for secondary alcohol etherification is a discovery of paramount importance in the present invention, insight gained into the kinetics and thermodynamics of the acid catalyzed etherification process has also led to a further discovery relating to increased selectivity of the process for symmetrical ether production. It has been discovered that the continuous removal during the process of essentially all of the olefin and ether produced by dehydration of alcohol results in an improved selectivity. This follows because the removal of olefin prevents acid catalyzed olefin hydration to produce an isomer of the starting alcohol while also eliminating the complicating reaction of olefin oligomerization. Since it has been discovered that the zeolite catalyzed etherification reaction proceeds at a faster rate that olefin hydration, removing olefin from the reaction mixture by distillation avoids the rehydration reaction of the olefin and contributes significantly to an increase in selectivity for the production of the symmetrical secondary ether of the starting secondary alcohol removing the di-secondary alkyl ether prevents the reverse reaction of this desired product.

While it is most convenient and preferable to remove the olefin and ether by distillation during the course of the etherification reaction, other means of olefin and ether removal known to those skilled in the art can also be utilized. A preferred method is to carry out the reaction by the known methods of catalytic distillation where the etherification catalyst particles comprising the etherification zone are contained within the distillation column. The etherification occurs in the catalytic bed of the distillation column with ether product returning to the distillation pot while olefin is removed overhead.

The method and advantages of the process of the invention are illustrated in the following examples.

EXAMPLE 1

Dicyclopentyl Ether Synthesis

A series of comparative experiments were carried out on the reaction of cyclopentanol over various acid catalysts to produce dicyclopentyl ether, cyclopentene and water. The activity and selectivity of zeolites Beta, ZSM-5, REY and HY were compared with a typical sulfonated resin catalyst (Amberlyst 15, Rohmand Haas). The results of the experiments show that the zeolites tested, particularly ZSM-5, are distinctly more selective for ether production than Amberlyst 15. The reaction conditions and results are tabulated in Table 1 as follows:

TABLE 1

| Catalyst | WHSV[1] | Cyclopentanol Conversion, % | Temp., °C., | Wt % Ether/ Wt % Cyclopentene[2] |
|---|---|---|---|---|
| Beta | 0.11 | 95 | 110 | 0.75 |
| ZSM-5 | 0.67 | 8 | 93 | 1.4 |
| Beta | 0.67 | 12 | 93 | 1.0 |
| REY | 0.67 | 8 | 93 | 0.25 |
| Amb. 15 | 0.56 | 80 | 117 | 0.05 |
| ZSM-5 | 0.56 | 85 | 117 | 0.65 |
| Beta | 0.56 | 88 | 117 | 0.79 |
| HY | 0.64 | 22 | 117 | 0.70 |

[1] weight cyclopentanol/(wt catalyst)(time)
[2] The weight ratio of dicyclopentyl ether to cyclopentene found in the product.

Table 1 shows that zeolite Beta converted cyclopentanol to ether at three different conversions, i.e., 95%, 88% and 12%. The zeolite catalyst produced a weight ratio of ether to olefin in the product of at least 0.20. These data show that not all large pore zeolites are good catalysts. Zeolite REY shows poor selectivity, although not as poor as Amberlyst-15 (Amb.15). The reason for the wide range of ether selectivity using zeolite catalyst is not fully understood and is unexpected. Nevertheless, it is evident that ZSM-5 is a superior catalyst for cyclopentanol etherification.

Due to the reversibility of all reactions in the process and the complex reaction network of hydration, dehydration, etherification, olefin isomerization and olefin oligomerization occurring in the process, the complete conversion of secondary alcohols to ethers is impossible. At high conversion, kinetic control of the process diminishes in favor of thermodynamics. However, it has been discovered that high selectivity is achieved when zeolite catalyst are used in a process that is maintained under kinetic control. Therefore, for the instant process it is preferred to avoid those reaction conditions where thermodynamics dominates the control of product distribution. Under thermodynamic controlling conditions the high selectivity realized with zeolite catalysts would be considerably reduced.

EXAMPLE 2

Five grams of cyclopentanol were refluxed at 135° C. over 1 gram of zeolite ZSM-5 catalyst particles in a short path distillation device. The cyclopentene formed in the reaction distilled out of the reaction zone and was thereby prevented from further reaction. The reflux was halted after sixteen hours at reflux when ninety percent of the alcohol was converted. Unreacted cyclopentanol was removed by extensive water washing. Three grams of product were recovered comprising greater than ninety-five weight percent dicyclopentyl ether.

The foregoing example demonstrates that the etherification reaction of secondary alcohols is controlled by reaction kinetics and that cyclopentanol reacts much faster that cyclopentene. As a result, selectivity for the production of the symmetrical ether from the starting alcohol can be improved by applying the expedient removal of cyclopentene from the reaction mixture as it is formed.

EXAMPLE 3

Six grams of 2-pentanol were refluxed over 1 gram of zeolite Beta catalyst extrudate for forty-eight hours in a short path distillation device. The pentene formed in the reaction distilled out of the reaction zone and was thereby prevented from further reaction. The di-secondary pentyl ether formed also distilled out of the reaction zone into the pot where it was protected from further react. Only the 2-pentanol remained in the reaction zone. The crude product was washed with water to remove unreacted alcohol. One gram of 2,2-di-sec-pentyl ether was recovered in over ninety-five percent purity. 2,3-di-sec-pentyl ether comprised about three weight percent of the product.

The foregoing example is a further specific illustration of the high selectivity for isomer production realized in the process of the instant invention.

EXAMPLE 4

Di-secondary alkyl ether synthesis was carried out according to the procedure of the invention using various secondary alcohols to illustrate the advantageous selectivity of the process of the invention. The reaction conditions and results are tabulated in Table 2.

TABLE 2

| | Di-Secondary Alkyl Ether Synthesis | | | | |
|---|---|---|---|---|---|
| Alcohol | Catalyst | Conv. % | Ether/ Olefin[a] | Temp. °C. | WHSV[b] |
| Sec-butanol | Zeo. Beta | 40 | 1.7 | 110 | 0.11 |
| 2-Hexanol | Zeo. Beta | 40 | 0.37 | 110 | 0.11 |
| 2-Pentanol | Zeo. Beta | 25 | 0.50 | 110 | 0.11 |
| Isopropanol | Zeo. Beta | 56 | 35 | 116 | 0.07 |
| Isopropanol | ZSM-5 | — | — | 116 | 0.05 |

[a] The only significant reaction products are di-secondary alkyl ether, olefin and water. For isopropanol, the products are DIPE, propylene and water and the column entry is wt % DIPE/wt % propylene.
[b] Weight alcohol/(wt catalyst)(time).

The process of the invention represents the first occasion where high yields of symmetrical ethers are obtained starting with $C_4+$ secondary alcohols and using acidic catalysts. The process offers an opportunity to prepare a wide range of secondary ethers simply and in high yield and selectivity wherein the weight ratio of ether to olefin in the product is at least 0.20.

What is claimed is:

1. A process for the production of $C_8+$ symmetrical secondary ethers with high selectivity by intermolecular dehydration of $C_4+$ secondary alkanol comprising:

contacting said alkanol with acidic solid, shape selective aluminosilicate zeolite catalyst particles selected from the group consisting of ZSM-5, zeolite Beta and zeolite Y in an etherification zone under etherification reaction conditions comprising temperature between 75° C. and 175° C. pressure between 15 psi (105 kPa) and 1000psi (7000 Kpa) and weight hourly space velocity (WHSV) between 0.01 and 1.0. whereby a reaction product is produced comprising said symmetrical ether of said alkanol, olefin by-product corresponding to the intramolecular dehydration product of said alkanol, unconverted alkanol and water; continuously separating said olefin by distillation from said reaction product during said etherification reaction; and recovering said ether having a weight ratio of said ether to said olefin of at least 0.37.

2. The process of claim 1 wherein said alkanol comprises cyclopentanol.

3. The process of claim 1 wherein said alkanol comprises secondary butanol.

4. The process of claim 1 wherein said alkanol comprises 2-hexanol.

5. The process of claim 1 wherein said alkanol comprises 2-pentanol.

6. The process of claim 1 wherein said etherification zone comprises a catalytic distillation reactor.

7. A process for the production of di-cyclopentyl ether with high selectivity by intermolecular dehydration of cyclopentanol, comprising:

contacting said cyclopentanol with ZSM-5 zeolite catalyst particles in an etherification zone under etherification reaction conditions comprising temperature between 75° C. and 175° C. whereby a reaction product is produced comprising said di-cyclopentyl ether, olefin by-product corresponding to the intramolecular dehydration product of said alkanol, unconverted alkanol and water; and separating said reaction product to recover said ether having a weight ratio of said ether to said olefin of at least 0.60 and cyclopentanol conversion of at least 80 weight percent.

8. The process of claim 7 wherein said etherification zone comprises a catalytic distillation reactor whereby said olefin by-product and said di-cyclopentyl ether are separated continuously and removed from said etherification zone.

9. The process of claim 1 wherein said secondary alkanol is selected from the group consisting of $C_4$–$C_{20}$ secondary alkanol.

* * * * *